(12) United States Patent
Raymond

(10) Patent No.: US 6,207,442 B1
(45) Date of Patent: Mar. 27, 2001

(54) PLASMID CONSTRUCTION BY HOMOLOGOUS RECOMBINATION

(75) Inventor: Christopher K. Raymond, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/173,043

(22) Filed: Oct. 15, 1998

Related U.S. Application Data

(60) Provisional application No. 60/062,061, filed on Oct. 16, 1997.

(51) Int. Cl.[7] ............... C12N 1/14; C12Q 1/68; C12P 21/06
(52) U.S. Cl. .......... 435/254.21; 435/6; 435/69.1
(58) Field of Search ............ 435/254.2, 254.21, 435/71.1, 69.7, 320.1, 69.4, 243, 325; 800/2; 536/23.51

(56) References Cited

U.S. PATENT DOCUMENTS 5,721,367 * 2/1998 Kay et al. ................. 800/2
5,989,866 * 11/1999 Deisher et al. ............ 435/69.4

FOREIGN PATENT DOCUMENTS

0288435A1 * 10/1988 (EP) .
97/07206    2/1997 (WO) .

OTHER PUBLICATIONS

Ma et al., "Plasmid construction by homologous recombination in yeast," 1987, Gene, 58, pp. 201–216.*
Hopp et al., "A Short Polypetide Marker Sequence Useful for Recombinant Protein Identification and Purification," 1988, Bio/Technology, vol. 6, pp. 1204–1210.*
Ma et al., *Gene* 58: 201–216, 1987.
Oldenburg et al., *Nucleic Acids Res.* 25: 451–452, 1997.
Patrusky, *Mosaic* 21: 44–52, 1990.
Pompon et al., *Gene* 83: 15–24, 1989.
Hudson, Jr. et al., *Genome Res.* 7: 1169–1173, 1997.

* cited by examiner

*Primary Examiner*—John S. Brusca
*Assistant Examiner*—Young Kim
(74) *Attorney, Agent, or Firm*—Gary E. Parker

(57) ABSTRACT

Methods for preparing double stranded, circular DNA molecules comprising a region encoding a protein of interest are disclosed. One or more donor DNA fragments encoding the protein of interest are combined with an acceptor plasmid, a first DNA linker, and a second DNA linker in a Saccharomyces cerevisiae host cell whereby the donor DNA fragment is joined to the acceptor plasmid by homologous recombination of the donor DNA, acceptor plasmid, and linkers to form the closed, circular plasmid.

14 Claims, 5 Drawing Sheets

SEQUENCE LISTING

<160> NUMBER OF SEQ ID NOS: 34

<210> SEQ ID NO 1
<211> LENGTH: 6
<212> TYPE: PRT
<213> ORGANISM: Artificial Sequence
<220> FEATURE:
<223> OTHER INFORMATION: peptide tag

<400> SEQUENCE: 1

Glu Tyr Met Pro Met Glu
 1               5

<210> SEQ ID NO 2
<211> LENGTH: 159
<212> TYPE: DNA
<213> ORGANISM: Artificial Sequence
<220> FEATURE:
<223> OTHER INFORMATION: plasmid segment

<400> SEQUENCE: 2
ttcgtttcgc ccagccagga aatccatgcc gagttccaac gcggccgtag agattataag      60
gatgatgatg ataagtacgt agactacaaa gacgacgacg acaaataatc tagaggatct     120
ggggtggcat ccctgtgacc cctccccagt gcctctcct                             159

<210> SEQ ID NO 3
<211> LENGTH: 153
<212> TYPE: DNA
<213> ORGANISM: Artificial Sequence
<220> FEATURE:
<223> OTHER INFORMATION: plasmid segment

<400> SEQUENCE: 3
ttcgtttcgc ccagccagga aatccatgcc gagttccaac gcggccgtag agaggagtat      60
atgcctatgg agtacgtaga agaatacatg cccatggaat aatctagagg atctggggtg     120
gcatccctgt gacccctccc cagtgcctct cct                                   153

<210> SEQ ID NO 4
<211> LENGTH: 141
<212> TYPE: DNA
<213> ORGANISM: Artificial Sequence
<220> FEATURE:
<223> OTHER INFORMATION: plasmid segment

<400> SEQUENCE: 4
agcttggaca agagagatta caaggacgat gatgacaagg gtggtcccgg gggtggtgac      60
tacaaggacg acgacgacaa gtagaattcc tagtattcta gggctgcctg tttggatatt     120
tttataattt ttgagagttt g                                                141

<210> SEQ ID NO 5
<211> LENGTH: 138
<212> TYPE: DNA
<213> ORGANISM: Artificial Sequence
<220> FEATURE:
<223> OTHER INFORMATION: plasmid segment

<400> SEQUENCE: 5
agcttggaca agagagaaga agaatacatg ccaatggaag gtggtcccgg gggaggcgag      60
gagtatatgc ctatggagta gaattcctag tattctaggg ctgcctgttt ggatattttt    120 ataattttg agagtttg                                                                138

<210> SEQ ID NO 6
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 6
gtttcgccca gccaggaaat ccatgccgag ttccaacgcg gccgt                                  45

<210> SEQ ID NO 7
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 7
ccgagttcca acgcggccgt agagattata aggatgatga tgataag                               47

<210> SEQ ID NO 8
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 8
ccgagttcca acgcggccgt agagaggagt atatgcctat ggag                                  44

<210> SEQ ID NO 9
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 9
aggagaggca ctggggaggg gtcacaggga tgccacccca gatcc                                 45

<210> SEQ ID NO 10
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 10
ggcactggag tggcaacttc cagggccagg agaggcactg gggagg                                46

<210> SEQ ID NO 11
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 11
tcgtccaacg actataaaga gggcaggctg tcctctaagc gtcacc                                46

<210> SEQ ID NO 12
<211> LENGTH: 47
<212> TYPE: DNA
<213> ORGANISM: Artificial Sequence

```
<220> FEATURE:
<223> OTHER INFORMATION: synthetic oligonucleotide

<400> SEQUENCE: 12
ggctgtcctc taagcgtcac cccgggatcg ccactgtgtt ggaattc        47

<210> SEQ ID NO 13
<211> LENGTH: 49
<212> TYPE: DNA
<213> ORGANISM: Artificial Sequence
<220> FEATURE:
<223> OTHER INFORMATION: synthetic oligonucleotide

<400> SEQUENCE: 13
atgccacccc agatcctcta gattatttgt cgtcgtcgtc tttgtagtc      49

<210> SEQ ID NO 14
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 14
atgccacccc agatcctcta gattattcca tgggcatgta ttcttc         46

<210> SEQ ID NO 15
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 15
ggcactgggg aggggtcaca gggatgccac cccagatcct ctaga          45

<210> SEQ ID NO 16
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 16
agcattgcta aagaagaagg tgtaagcttg gacaagagag a              41

<210> SEQ ID NO 17
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 17
ggtgtaagct tggacaagag agaagaagaa tacatgccaa tggaaggtgg t   51

<210> SEQ ID NO 18
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 18
tggcaaactc tcaaaaatta taaaaatatc caaacaggca gccgaattct a   51
```

<210> SEQ ID NO 19
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 19
atcatagaag agaaaaacat tagttggcaa actctcaaaa attataaaaa ta                52

<210> SEQ ID NO 20
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 20
acggtttatt gtttatcaat actactattg ctagcattgc                              40

<210> SEQ ID NO 21
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 21
tcaatactac tattgctagc attgctgcta agaagaagg tgtaagcttg gacaagagag          60
aa                                                                       62

<210> SEQ ID NO 22
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 22
aacaggcagc cctagaatac taggaattct actccatagg catatactcc tcgcctcc          58

<210> SEQ ID NO 23
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 23
attataaaaa tatccaaaca ggcagcccta gaatactag                               39

<210> SEQ ID NO 24
<211> LENGTH: 917
<212> TYPE: DNA
<213> ORGANISM: Homo sapiens
<220> FEATURE:
<221> NAME/KEY: CDS
<222> LOCATION: (1)...(624)

<400> SEQUENCE: 24 atg tat tca gcg ccc tcc gcc tgc act tgc ctg tgt tta cac ttc ctg          48
Met Tyr Ser Ala Pro Ser Ala Cys Thr Cys Leu Cys Leu His Phe Leu
 1               5                  10                  15 ctg ctg tgc ttc cag gta cag gtg ctg gtt gcc gag gag aac gtg gac          96
Leu Leu Cys Phe Gln Val Gln Val Leu Val Ala Glu Glu Asn Val Asp -continued

```
                20                  25                  30
ttc cgc atc cac gtg gag aac cag acg cgg gct cgg gac gat gtg agc    144
Phe Arg Ile His Val Glu Asn Gln Thr Arg Ala Arg Asp Asp Val Ser
         35                  40                  45 cgt aag cag ctg cgg ctg tac cag ctc tac agc cgg acc agt ggg aaa    192
Arg Lys Gln Leu Arg Leu Tyr Gln Leu Tyr Ser Arg Thr Ser Gly Lys
 50                  55                  60 cac atc cag gtc ctg ggc cgc agg atc agt gcc cgc ggc gag gat ggg    240
His Ile Gln Val Leu Gly Arg Arg Ile Ser Ala Arg Gly Glu Asp Gly
 65                  70                  75                  80 gac aag tat gcc cag ctc cta gtg gag aca gac acc ttc ggt agt caa    288
Asp Lys Tyr Ala Gln Leu Leu Val Glu Thr Asp Thr Phe Gly Ser Gln
                 85                  90                  95 gtc cgg atc aag ggc aag gag acg gaa ttc tac ctg tgc atg aac cgc    336
Val Arg Ile Lys Gly Lys Glu Thr Glu Phe Tyr Leu Cys Met Asn Arg
            100                 105                 110 aaa ggc aag ctc gtg ggg aag ccc gat ggc acc agc aag gag tgt gtg    384
Lys Gly Lys Leu Val Gly Lys Pro Asp Gly Thr Ser Lys Glu Cys Val
        115                 120                 125 ttc atc gag aag gtt ctg gag aac aac tac acg gcc ctg atg tcg gct    432
Phe Ile Glu Lys Val Leu Glu Asn Asn Tyr Thr Ala Leu Met Ser Ala
    130                 135                 140 aag tac tcc ggc tgg tac gtg ggc ttc acc aag aag ggg cgg ccg cgg    480
Lys Tyr Ser Gly Trp Tyr Val Gly Phe Thr Lys Lys Gly Arg Pro Arg
145                 150                 155                 160 aag ggc ccc aag acc cgg gag aac cag cag gac gtg cat ttc atg aag    528
Lys Gly Pro Lys Thr Arg Glu Asn Gln Gln Asp Val His Phe Met Lys
                165                 170                 175 cgc tac ccc aag ggg cag ccg gag ctt cag aag ccc ttc aag tac acg    576
Arg Tyr Pro Lys Gly Gln Pro Glu Leu Gln Lys Pro Phe Lys Tyr Thr
            180                 185                 190 acg gtg acc aag agg tcc cgt cgg atc cgg ccc aca cac cct gcc tag    624
Thr Val Thr Lys Arg Ser Arg Arg Ile Arg Pro Thr His Pro Ala
        195                 200                 205 gccacccgc cgcggccctc aggtcgccct ggccacactc acactcccag aaaactgcat    684
cagaggaata tttttacatg aaaaataagg attttattgt tgacttgaaa ccccccgatga   744 caaaagactc acgcaaaggg actgtagtca acccacaggt gcttgtctct ctctaggaac    804
agacaactct aaactcgtcc ccagaggagg acttgaatga ggaaaccaac actttgagaa    864
accaaagtcc tttttcccaa aggttctgaa aaaaaaaaa aaaaaaactc gag             917
```

<210> SEQ ID NO 25
<211> LENGTH: 207
<212> TYPE: PRT
<213> ORGANISM: Homo sapiens

<400> SEQUENCE: 25

```
Met Tyr Ser Ala Pro Ser Ala Cys Thr Cys Leu Cys Leu His Phe Leu
 1               5                  10                  15

Leu Leu Cys Phe Gln Val Gln Val Leu Val Ala Glu Glu Asn Val Asp
                20                  25                  30

Phe Arg Ile His Val Glu Asn Gln Thr Arg Ala Arg Asp Asp Val Ser
            35                  40                  45

Arg Lys Gln Leu Arg Leu Tyr Gln Leu Tyr Ser Arg Thr Ser Gly Lys
        50                  55                  60

His Ile Gln Val Leu Gly Arg Arg Ile Ser Ala Arg Gly Glu Asp Gly
 65                  70                  75                  80
```

```
Asp Lys Tyr Ala Gln Leu Leu Val Glu Thr Asp Thr Phe Gly Ser Gln
             85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
            115                 120                 125

Phe Ile Glu Lys Val Leu Glu Asn Asn Tyr Thr Ala Leu Met Ser Ala
            130                 135                 140

Lys Tyr Ser Gly Trp Tyr Val Gly Phe Thr Lys Gly Arg Pro Arg
145                 150                 155                 160

Lys Gly Pro Lys Thr Arg Glu Asn Gln Gln Asp Val His Phe Met Lys
            165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
            195                 200                 205
```

<210> SEQ ID NO 26
<211> LENGTH: 63
<212> TYPE: DNA
<213> ORGANISM: Artificial Sequence
<220> FEATURE:
<223> OTHER INFORMATION: synthetic oligonucleotide

<400> SEQUENCE: 26
ggtgtaagct tggacaagag agaggagaac gtggacttcc gcatccacgt ggagaaccag    60
acg                                                                 63

<210> SEQ ID NO 27
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 27
cagccgcagc tgcttagcgc tcacatcgtc ccgagcccgc gtctggttct ccacgtggat    60
gc                                                                  62

<210> SEQ ID NO 28
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 28
ccggctgtag agctggtaca gccgcagctg cttacggct                           39

<210> SEQ ID NO 29
<211> LENGTH: 141
<212> TYPE: DNA
<213> ORGANISM: Artificial Sequence
<220> FEATURE:
<223> OTHER INFORMATION: DNA linker

<400> SEQUENCE: 29
agcattgctg ctaaagaaga aggtgtaagc ttggacaaga gagaggagaa cgtggacttc    60
cgcatccacg tggagaacca gacgcgggct cgggacgatg tgagccgtaa gcagctgcgg   120
ctgtaccagc tctacagccg g                                            141

```
<210> SEQ ID NO 30
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 30
cttcagaagc ccttcaagta cacgacggtg accaagaggt cc                42

<210> SEQ ID NO 31
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 31
acgacggtga ccaagaggtc ccgtcggatc cggcccacac accctgccta gggggaattc   60
g                                                                  61

<210> SEQ ID NO 32
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 32
caaacaggca gccctagaat actagtgtcg actcgaggat ccgaattccc cctaggcagg   60
g                                                                  61

<210> SEQ ID NO 33
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 33
ctcaaaaatt ataaaaatat ccaaacaggc agccctagaa tact                   44

<210> SEQ ID NO 34
<211> LENGTH: 144
<212> TYPE: DNA
<213> ORGANISM: Artificial Sequence
<220> FEATURE:
<223> OTHER INFORMATION: DNA linker

<400> SEQUENCE: 34
cttcagaagc ccttcaagta cacgacggtg accaagaggt cccgtcggat ccggcccaca   60
caccctgcct aggggaatt cggatcctcg agtcgacact agtattctag ggctgcctgt   120
ttggatattt ttataatttt tgag                                        144
```

PLASMID CONSTRUCTION BY HOMOLOGOUS RECOMBINATION

CROSS-REFERENCE TO RELATED APPLICATION

This application claims the benefit under 35 U.S.C. § 119(e) of provisional application Ser. No. 60/062,061, filed Oct. 16, 1997.

BACKGROUND OF THE INVENTION

Recombinant DNA technology is now widely used for both research and commercial protein production. An essential tool of this technology is the plasmid, a double-stranded DNA molecule that can replicate (autonomously or by chromosomal integration) in one or more species of host cell. A DNA sequence of interest can be inserted into a plasmid and replicated in large quantities. If a sequence encoding a protein is operably linked to a transcription promoter, the sequence can be expressed and the encoded protein can be recovered from the cell.

DNA sequences of interest are commonly joined to plasmids by cutting both pieces of DNA with a restriction endonuclease to provide complementary ends that are then enzymatically ligated together. If the sequences of the two pieces do not permit the use of a single restriction endonuclease, small oligonucleotide adapters can be used to join the free ends.

Advances in recombinant DNA technology, including the use of automation, have resulted in the rapid identification and production of novel DNA sequences. To further characterize these sequences it is necessary to express them and study the properties of the encoded proteins. Expression generally requires the precise joining of DNA sequences within expression vectors to maintain the functional relationships between genetic elements (e.g., open reading frame, promoter function, etc.). Current methods, which rely primarily on the use of restriction enzymes, can be problematic when it is necessary to rapidly express a large number of sequences and analyze their products because these methods can require extensive and time-consuming manipulation of sequences to obtain the desired junctions. There is thus a need in the art for improved methods of plasmid construction. Toward this end, the present invention provides a standardized plasmid into which a variety of DNA sequences can be readily inserted and subsequently expressed, as well as related cloning methods and other improvements.

SUMMARY OF THE INVENTION

The invention provides a universal acceptor plasmid that can be used to clone a DNA encoding any polypeptide of interest, including polypeptide fusions. The acceptor plasmid is useful within methods for preparing double stranded, circular DNA molecules. One such method comprises the steps of: (a) providing a double-stranded donor DNA fragment encoding a polypeptide of interest; (b) providing a double-stranded, linear acceptor plasmid having blunt first and second ends and comprising a selectable marker and replication sequence that are functional in *Saccharomyces cerevisiae*, wherein the acceptor plasmid is essentially free of DNA encoding the polypeptide of interest; (c) providing a first double-stranded DNA linker comprising a first segment identical in sequence to a first region of the acceptor plasmid and a second segment identical in sequence to a first region of the donor DNA fragment, wherein each of the first and second segments of the first linker is at least 10 bp in length, preferably at least 50 bp in length; (d) providing a second double-stranded DNA linker comprising a first segment identical in sequence to a second region of the acceptor plasmid and a second segment identical in sequence to a second region of the donor DNA fragment, wherein each of the first and second segments of the second linker is at least 10 bp in length, preferably at least 50 bp in length; and (e) combining the donor DNA fragment, acceptor plasmid, first DNA linker, and second DNA linker in a *Saccharamyces cerevisiae* host cell whereby the donor DNA fragment is joined to the acceptor plasmid by homologous recombination of the donor DNA, acceptor plasmid, and linkers to form a closed, circular plasmid comprising a region encoding the polypeptide of interest. Within one embodiment of the invention, the acceptor plasmid further comprises a transcription promoter proximal to the first end, and the donor DNA fragment is operably linked to the transcription promoter within the closed, circular plasmid. Within a related embodiment, the acceptor plasmid further comprises a transcription terminator proximal to the second end, and the donor DNA fragment is operably linked to the transcription terminator within the closed, circular plasmid. Within other embodiments, the acceptor plasmid further comprises a DNA segment encoding a leader peptide and/or one or more DNA segments encoding a peptide tag, positioned such that these DNA segments are operably linked to the donor DNA fragment within the closed, circular plasmid. Within a preferred embodiment, the acceptor plasmid further comprises (a) a promoter, a DNA segment encoding a leader peptide, and a DNA segment encoding a first peptide tag, wherein the DNA segment encoding a leader peptide is positioned between the promoter and the DNA segment encoding a first peptide tag proximal to the first end of the acceptor plasmid, and wherein the promoter, DNA segment encoding a leader peptide, and DNA segment encoding a first peptide tag are operably linked; and (b) a DNA segment encoding a second peptide tag proximal to the second end of the acceptor plasmid.

A related aspect of the invention provides a method for preparing a double stranded, circular DNA molecule comprising the steps of: (a) providing a plurality of overlapping, double-stranded donor DNA fragments which collectively encode a polypeptide of interest; (b) providing a double-stranded, linear acceptor plasmid having blunt first and second ends and comprising a selectable marker and replication sequence that are functional in *Saccharamyces cerevisiae*, wherein the acceptor plasmid is essentially free of DNA encoding the polypeptide of interest; (c) providing a first double-stranded DNA linker comprising a first segment identical in sequence to a first region of the acceptor plasmid and a second segment identical in sequence to a region of one of the donor DNA fragments, wherein each of the first and second segments of the first linker is at least 10 bp in length, preferably at least 50 bp in length; (d) providing a second double-stranded DNA linker comprising a first segment identical in sequence to a second region of the acceptor plasmid and a second segment identical in sequence to a region of another of the donor DNA fragments, wherein each of the first and second segments of the second linker is at least 10 bp in length, preferably at least 50 bp in length; and (e) combining the donor DNA fragments, acceptor plasmid, first DNA linker, and second DNA linker in a *Saccharamyces cerevisiae* host cell whereby the donor DNA fragments are joined to the acceptor plasmid by homologous recombination of the donor DNA fragments, acceptor plasmid and linkers to form a closed, circular plasmid comprising a region encoding the polypeptide of interest. Within certain embodiments of the invention, the acceptor plasmid further comprises one or more of a transcription promoter, a transcription terminator, a DNA segment encoding a leader peptide, and one or more DNA segments encoding a peptide tag, as disclosed above.

These and other aspects of the invention will become evident upon reference to the following detailed description and figures.

DETAILED DESCRIPTION OF THE INVENTION

Figure 1:
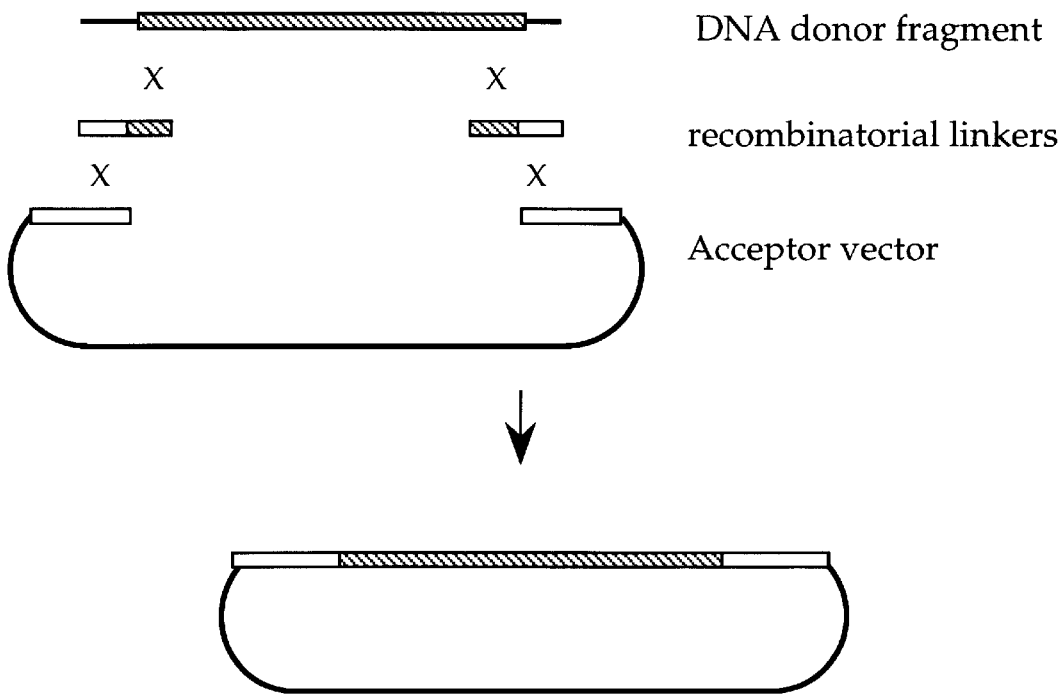
FIG. 1 illustrates the insertion of a donor DNA fragment into an acceptor vector.

Prior to describing the invention in more detail, certain terms used herein will be defined.

An "acceptor plasmid" (or "acceptor vector") is a plasmid or vector that carries sequences that permit replication in a host cell. For replication in yeast host cells, the acceptor plasmid will contain CEN, ARS or 2-micron sequences. For replication in *E. coli*, the acceptor plasmid will contain ori or other suitable bacterial replication sequences. For selection in yeast, the acceptor plasmid will contain a selectable marker, such as the URA3 sequence or other marker as disclosed below; for selection in *E. coli*, it may contain an antibiotic resistance marker (e.g., Amp$^R$) or a prototrophic marker (e.g., Trp).

As used herein, a "donor DNA fragment" is a double-stranded DNA fragment or molecule that encodes at least a portion of a polypeptide of interest. The DNA donor fragment may be heterologous or homologous to the expression host cell. A heterologous DNA fragment does not exist naturally within a given host cell. A homologous DNA fragment exists naturally within a given host cell. DNA molecules heterologous to a particular host cell may contain DNA derived from the host cell species, so long as that host DNA is combined with non-host DNA. For example, a DNA molecule containing a non-host DNA segment encoding a polypeptide operably linked to a host DNA segment comprising a transcription promoter is considered to be a heterologous DNA molecule.

A plasmid is "essentially free" of DNA encoding a polypeptide of interest when it contains less than ten contiguous nucleotides encoding the polypeptide of interest.

"Homologous recombination" is genetic recombination, mediated by host cell enzymes, that depends upon a substantial degree of homology (the longer the better) between the DNA sequences involved.

"Homology" is used in its common sense to denote degree of identity between amino acid or nucleotide sequences. "Sequence homology" and "sequence identity" are used interchangeably in the art.

A "leader peptide" is an amino acid sequence (usually about 15–100 amino acids) that is involved in directing secretion of a mature polypeptide or protein from a cell. Leader peptides are also called signal or secretory peptides, secretory leaders, prepro peptides and pre peptides. More specifically, a leader peptide directs translocation of a polypeptide or protein across the endoplasmic reticulum membrane (the entry to the secretory pathway) or across a bacterial cell membrane. Additional sequences in the leader assist transit through the secretory pathway in poorly understood ways and may also be essential to proper post-translational processing and transport of the polypeptide. Leader peptides are characterized by a core of hydrophobic amino acids and are typically (but not exclusively) found at the amino termini of newly synthesized proteins. Very often the leader peptide is cleaved from the mature protein during secretion in one or more cleavage events. Such leader peptides contain processing sites that allow cleavage of the leader peptides from the mature proteins as they pass through the secretory pathway or the bacterial cell membrane. An "amino-terminal leader sequence" is a DNA sequence encoding a leader peptide that occurs at the amino terminus of a protein. An exemplary leader peptide used within the present invention is derived from *Saccharamyces cerevisiae* mating pheromone α-factor.

"Operably linked" indicates that polynucleotide segments are arranged so that they function in concert for their intended purposes, e.g., transcription initiates in the promoter and proceeds through the coding segment to the terminator.

A "peptide tag" (or "affinity tag") is a polypeptide (frequently, but not necessarily, relatively small) that is attached to the N- or C-terminus of a second polypeptide through recombinant technology, forming a fusion protein. The peptide tag often facilitates purification of the second polypeptide. Exemplary peptide tags include FLAG™ tags (Eastman Kodak Co., New Haven, Conn.; Hopp et al., *Bio/Technology* 6:1204–10, 1988), Glu-Glu tags (Glu-Tyr-Met-Pro-Met-Glu; SEQ ID NO:1) (Grussenmeyer et al., *Proc. Natl. Acad. Sci. USA* 82:7952–4, 1985), polyhistidine, protein A, glutathione S transferase, substance P, maltose binding protein, an immunoglobulin Fc polypeptide, and others. Criteria for selecting a peptide tag for a particular application will be apparent to those skilled in the art.

A genetic element is "proximal to" one end of a larger polynucleotide molecule when it is substantially closer to that end than to the other end. Within the present invention, the ends of a linear acceptor plasmid are joined, via homologous recombination, to a donor DNA encoding a polypeptide of interest. A promoter, terminator, or other genetic element proximal to one end of the linear acceptor plasmid is close enough to that end so as to become operably linked to the donor DNA upon recombination. Hence, proximity is defined relative to the function of the particular element and the composition of the acceptor plasmid. For example, a promoter will be considered to be proximal to the end of the linear acceptor plasmid if it is operably linked to a secretory signal sequence and amino-terminal peptide tag sequence whereby, upon recombination with the donor DNA, the promoter, secretory signal sequence, peptide tag sequence, and donor DNA form a functional expression cassette. In general, promoters will be positioned in acceptor plasmids so that the approximate position of the initiation ATG in the promoter's source gene is maintained in the resulting expression cassette.

A "recombinatorial linker" is a double-stranded oligonucleotide linker that shares sequence homology or sequence identity with a donor DNA fragment on one end, and with an acceptor plasmid on the other end.

A "segment" of a polynucleotide is a portion of a larger polynucleotide molecule having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

A "transcription promoter" is the portion of a gene at which RNA polymerase binds and mRNA synthesis is initiated. The promoter may also contain sites for the binding of regulatory proteins.

"Transformation", "transform", and "transformed" denote the process of introducing exogenous DNA into a host cell and the resulting presence in the host cell of the introduced DNA. The term is used broadly to encompass the introduction of a variety of DNA constructs into prokaryotic and eukaryotic cells. Transformation of cultured mammalian cells is commonly referred to as "transfection".

All references cited herein are incorporated by reference in their entirety.

The present invention provides an acceptor plasmid useful within methods for constructing double-stranded, closed circular DNA molecules through homologous recombination in yeast. In the yeast *Saccharomyces cerevisiae*, double-stranded breaks in DNA stimulate a DNA repair pathway that acts through homologous recombination. When a linearized acceptor plasmid is co-transformed with one or more donor DNA fragments and two oligonucleotide linkers into an appropriate yeast host cell, the DNA repair and plasmid replication abilities of the yeast host cell provide assembly of closed, circular plasmids through homologous recombination. The joining of the donor DNA fragment(s) to the linearized acceptor plasmid depends on sufficient overlap and sequence homology among the respective polynucleotide segments.

Hence, transforming DNA fragments that share at least 10, preferably at least 50, base pairs of overlapping identical sequence can undergo joining via recombination. Furthermore, linear DNA fragments cannot replicate in yeast, while circular DNAs carrying the appropriate replication and selection sequences can replicate and be maintained within the cell population. The appropriate sequences include: (1) replication sequences, either (a) an autonomously replicating sequence (ARS) to provide DNA replication with each cell cycle used in combination with a centromere sequence (CEN) that ensures equal partitioning of the plasmid DNA between dividing cells, or (b) replication sequences from the yeast 2-micron plasmid; and (2) a selectable marker, such as the URA3 biosynthetic gene, for selection of cells carrying the plasmid. It is preferred to further include a replication sequence and a selectable marker that function in an *E. coli* host to allow replication of the plasmid in *E. coli*, such as during construction of the acceptor plasmid or for amplification. If linear DNA segments that share the appropriate overlapping sequences are cotransformed into yeast, they can undergo recombination to form autonomously replicating circular DNAS. These features of DNA repair and plasmid replication in yeast can be used for plasmid assembly; an example of subcloning of a donor DNA fragment into a vector is shown in FIG. 1.

In the subcloning scheme of FIG. 1, there are three DNA components required for plasmid assembly. These are the DNA fragment(s) to be subcloned (donor fragment(s)), the acceptor vector into which the DNA is to be subcloned (e.g., an expression vector), and "recombinatorial linkers" that share sequence overlap and sequence homology with the acceptor vector on one end and the donor fragment(s) on the other. In a typical procedure, 100 ng of linearized acceptor vector from a 0.2–1.0 μg/μl solution is combined with approximately 1 μg of the donor DNA fragment from a 0.2–1.0 μg/μl solution and 1 μg of each linker.

The donor DNA is a single DNA fragment or a plurality of fragments encoding a polypeptide of interest. In general, the donor fragment(s) will typically be prepared in a conventional cloning vector and excised from the vector, although the invention is not limited to donor DNAs from any particular source. To minimize recombination artifacts, the donor DNA is liberated from the cloning vector on both ends by restriction digestion. Gel purification of the donor DNA fragment away from the vector is not necessary.

In general, an acceptor plasmid comprises yeast replication elements (CEN+ARS or 2-micron) and a selectable marker (e.g., URA3). It is preferred to include *E. coli* replication and marker elements (e.g., $Amp^R$ and ori) and a blunt-ended cloning site. The requirement for a blunt-ended cloning site is not absolute; however, the background of false positives increases by roughly 10-fold when cohesive restriction sites are used to linearize the acceptor vector.

The linkers are double-stranded DNA segments that share sequence identity on one end with vector sequences and identity on the other end with the donor DNA. The regions of identity are at least 10 bp, preferably at least 50 bp, in length. Within a preferred embodiment (illustrated in FIG. 2), the final linkers are generally ~140 bp, corresponding to 70 bp of sequence overlap on each end with the acceptor vector and donor DNA, respectively. Considerable flexibility is permitted in the internal region of a recombinatorial linker. It is possible to insert or delete specific sequences in the central region of the linker between the sequences that overlap the vector and cDNA. This flexibility can be used, for example, to introduce restriction sites or to add specific amino acid residues in these junctions.

Figure 2:
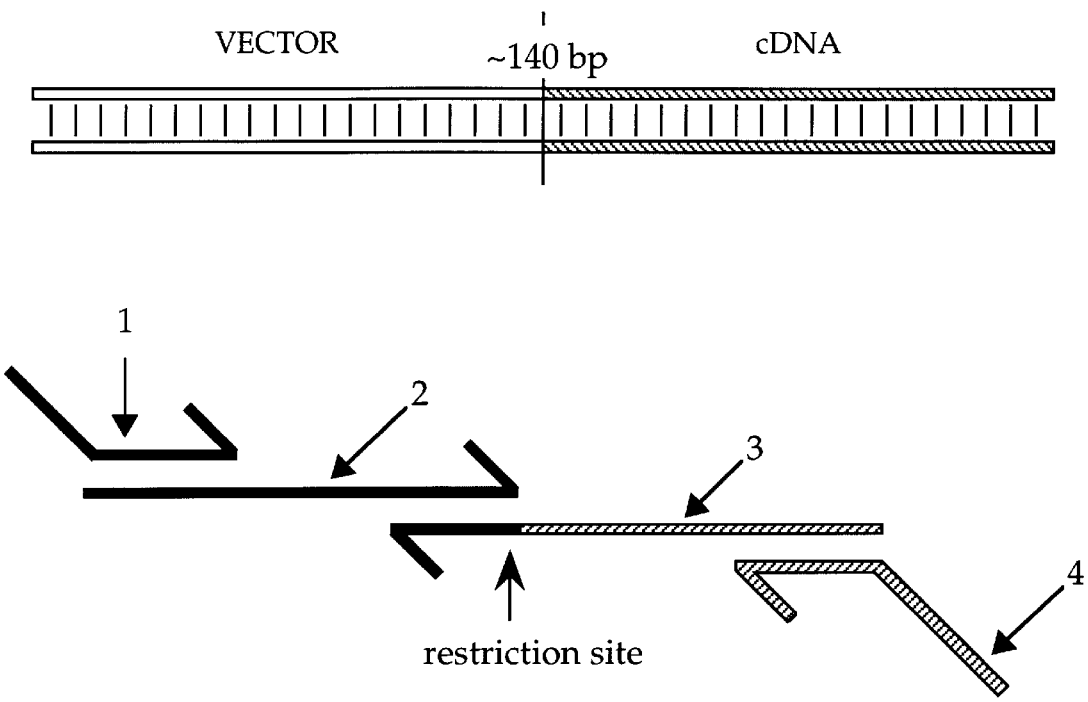
FIG. 2 illustrates oligonucleotides 2 and 3 and primers 1 and 4 used to assemble recombinatorial linkers.
Figure 3:
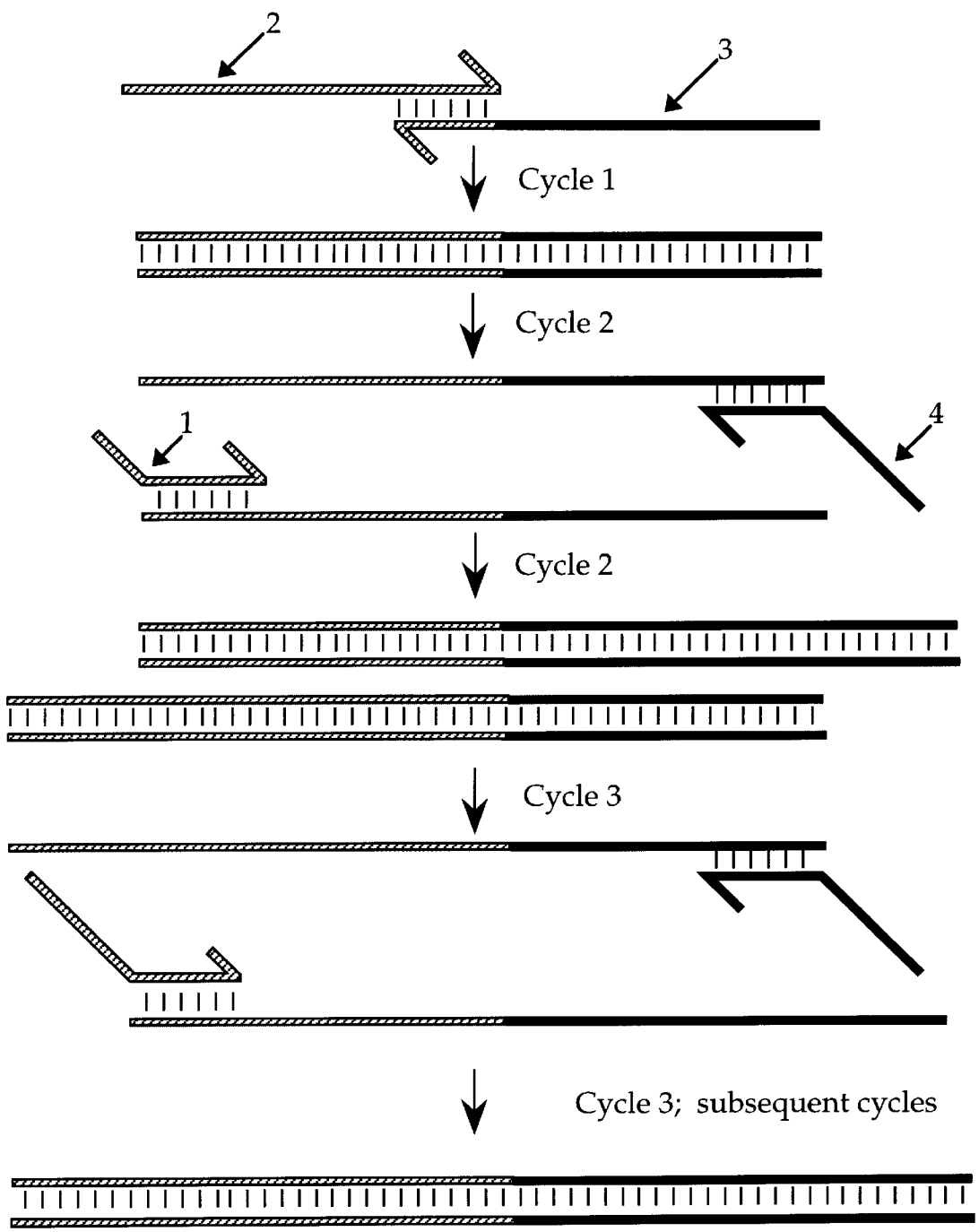
FIG. 3 illustrates PCR reactions that generate recombinatorial linkers.

The linkers are generated by conventional methods, preferably from oligonucleotides by PCR (polymerase chain reaction; Mullis, U.S. Pat. No. 4,683,202). A preferred method of linker construction is shown in FIG. 2 and FIG. 3. Lengths of oligonucleotides and primers is this example are preferred lengths. FIG. 2 illustrates four oligonucleotides used to generate a typical linker of about 140 bp, comprising about 70 bp homologous with the acceptor vector and about 70 bp homologous with the donor DNA. The common primer 1 is about 45 bp in length and overlaps with the common oligonucleotide 2 with Tm=68° C. (2° C. for A:T and 4° C. for G:C). In this example, the common oligonucleotide is also about 45 bp in length The common primer and common oligonucleotide provide the homology to the acceptor vector. These homologous sequences can be standardized to permit the insertion of any donor DNA into a single acceptor vector or family of acceptor vectors that share a "common" recombinatorial sequence. The donor DNA-specific oligonuceotide 3 is about 55 bp in length and overlaps with the common oligonucleotide 2 with Tm=68° C. As shown in FIG. 2, the donor DNA-specific oligonucleotide can be designed to include a restriction site at the junction between vector and donor DNA homology regions. Such a restriction site provides several advantages that will be evident to those skilled in the art, including a diagnostic tool for screening the resulting constructs and an additional restriction site for subsequent manipulations of the donor DNA. The donor DNA-specific primer 4 is about 55 bp in length and overlaps with oligonucleotide 3 with Tm=68° C. Double-stranded DNA linkers are generated by PCR as shown in FIG. 3. The common oligonucleotide 2 and the donor DNA-specific oligonucleotide 3 are first annealed and extended to generate a double-stranded, internal segment of the final linker. The double-stranded segment (about 100 bp in this example) is then denatured, the component strands are combined with the two primers, and the linker is extended and amplified by multiple cycles of PCR. Primers 1 and 4 comprise "tails" of an additional 20 base pairs and provide for both the amplification of the initial product and the extension of the sequence outward to its final length (e.g., 140 base pairs).

Figure 4:
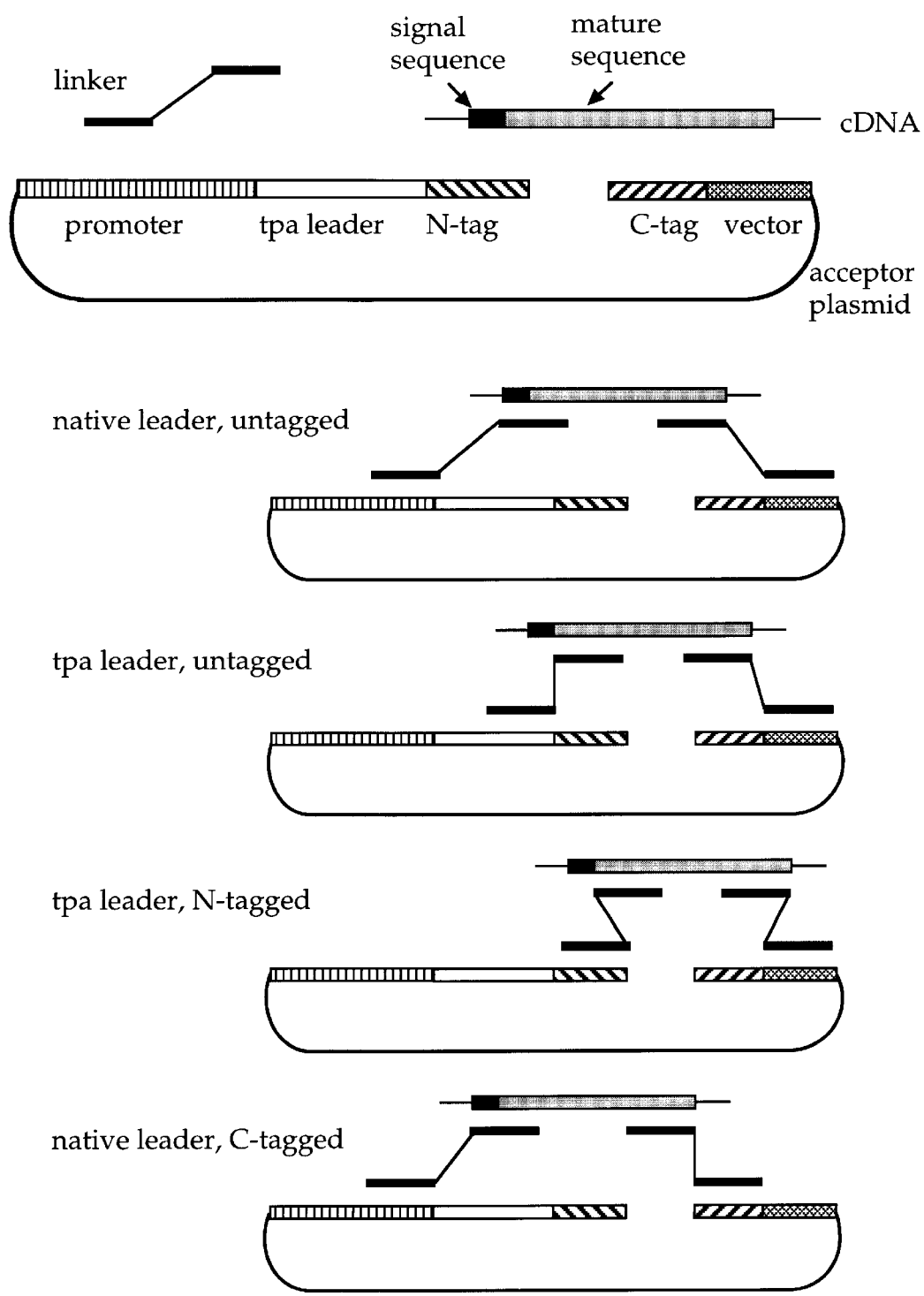
FIG. 4 illustrates methods for the construction of expression vectors for secretion of proteins of interest.

For plasmid assembly in yeast, the DNA donor fragment (s), the acceptor plasmid, and the two linkers are combined and co-transformed into yeast cells having a mutation requiring complementation by the selectable marker (e.g., ura$^-$ cells are transformed with a plasmid comprising the URA3 marker). Yeast cells harboring recombinant circular plasmids proliferate under selective conditions. For example, yeast cells transformed to become Ura$^+$ are selected on plates lacking uracil. Plasmid DNA is prepared from the transformed yeast cells and shuttled into *E. coli*. Conventional screening methods are then used to identify the appropriate plasmid constructs among *E. coli* transformants, which are selected on the basis of, for example, antibiotic resistance or prototrophy. Several examples of plasmid construction are illustrated in FIG. 4.

Figure 5:
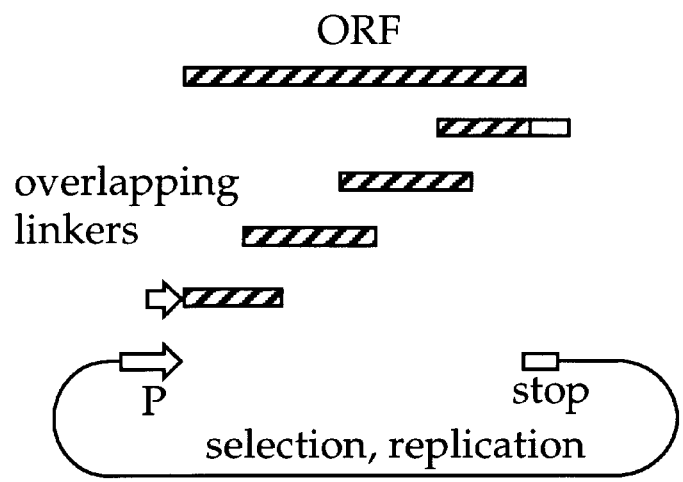
FIG. 5 illustrates an embodiment of the invention wherein a plurality of donor DNA fragments are joined to an acceptor vector.

Within one embodiment of the invention, the polypeptide of interest is encoded by a plurality of donor DNA fragments which, when recombined, collectively provide the coding sequence. This embodiment is illustrated in FIG. 5. This embodiment of the invention includes the use of a plurality of chemically synthesized DNA fragments or a combination of chemically synthesized DNA fragments and fragments of other origin, such as cloned cDNA.

Recombinatorial subcloning according to the present invention has several advantages. The primary advantage is that any vector sequence can be joined to any donor DNA sequence without the constraint of available restriction enzyme sites. Furthermore, plasmid assembly is technically simple; DNA fragments are simply mixed together prior to transformation. Finally, yeast recombination occurs with high fidelity, and thus regions of donor DNAs outside of the linker sequences are not subjected to error-generating processes.

When a DNA sequence encoding a polypeptide of interest is incorporated into a closed, circular plasmid through the methods of the present invention, the resultant plasmid is suitable for production of the polypeptide of interest. If the closed, circular plasmid includes a heterologous secretory leader peptide in combination with the polypeptide of interest, the respective DNA segments are joined in the correct reading frame so that the joined segments encode a fusion protein. The joined secretory leader and polypeptide of interest will typically define a proteolytic cleavage site at their junction, so that the secretory leader is removed from the polypeptide of interest during secretion. Additional proteolytic sites can also be provided, such as between components of fusion protein, between a protein of interest and an affinity tag, etc. Those skilled in the art will recognize that a protein can be recovered and subsequently processed in vitro, such as to release the protein of interest from an affinity tag used in purification or to convert a protein of interest from a precursor to its mature, active form.

The methods of the present invention can be used to insert a single donor DNA fragment into a plasmid, or to assemble a plurality of donor DNA fragments in a plasmid. In the latter case, the assembled fragments can encode a single protein (or a fragment of a single protein), or can encode a fused polypeptide that comprises portions from a plurality of source proteins. Fused polypeptides may further comprise engineered cleavage sites, spacers, or other desired amino acid sequences, including peptide tags as disclosed above. In principle, the nucleotide sequences of donor fragments are constrained only by the genetic code; essentially any DNA sequence encoding the polypeptide of interest can be used. Those skilled in the art will recognize, however, that in practice it is often advantageous to design donor sequences to include or exclude certain codons or sequences. For example, a donor sequence can be designed to contain (or not to contain) specific sub-sequences, such as restriction endonuclease recognition sites. Donor sequences can also be designed to reflect codon usage preferences of the host cell. It is also advantageous to minimize sequence identity between a donor DNA fragment and the acceptor plasmid to avoid unwanted recombinatorial events. In this regard it is preferred to avoid regions of sequence identity of 50 bp or more, preferably avoiding sequence identities of 10 bp or more. It will also be recognized that sequences of multiple donor DNA fragments can be engineered to avoid unwanted recombinatorial events among those donor fragments.

Suitable host cells for expression of the polypeptide of interest are those cell types that can be transformed with exogenous DNA and grown in culture, and include bacteria, fungal cells, and cultured higher eukaryotic cells (including, but not limited to, mammalian cells and insect cells). Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989; Murray (ed.), *Gene Transfer and Expression Protocols*, Humana Press, Clifton, N.J., 1991; Glick and Pasternak, *Molecular Biotechnology: Principles and Applications of Recombinant DNA*, ASM Press, Washington, D.C., 1994; Ausubel et al. (eds.), *Short Protocols in Molecular Biology*, 3rd edition, John Wiley and Sons, Inc., New York, 1995; Wu et al., *Methods in Gene Biotechnology*, CRC Press, New York, 1997.

Those skilled in the art will recognize that expression vectors are ordinarily prepared with a particular host cell, or combination of host cells, in mind. These design criteria also apply to the acceptor plasmids of the present invention. For example, if one is intending to use the product plasmid for expressing the polypeptide of interest in a cultured mammalian cell, the acceptor plasmid will comprise a promoter that functions in the cultured mammalian cell, and may also contain such additional genetic elements as a selectable marker, an enhancer, splice sites, etc. Within another example, a vector for use in Pichia methanolica will comprise a *P. methanolica* promoter, selectable marker, etc. as disclosed in more detail below. As noted above, it is common practice in the art to include a bacterial origin of replication and a bacterial selectable marker to allow replication of the vector in a prokaryotic host. In certain instances these bacterial sequences may be excised from the vector prior to transformation into the final host. Construction of expression vectors for use in a predetermined species of host cell is routine in the art, and many such vectors and vector components can be purchased from commercial suppliers.

The methods of the present invention can be used to produce plasmids, including expression vectors, comprising inserts encoding proteins of research, industrial, or pharmaceutical interest. Such proteins include enzymes such as lipases, cellulases, and proteases; enzyme inhibitors, including protease inhibitors; growth factors such as platelet derived growth factor, fibroblast growth factors, and epidermal growth factor; cytokines such as erythropoietin, thrombopoietin, colony stimulating factors, and interleukins; and hormones such as insulin, proinsulin, leptin, and glucagon.

Yeast cells, particularly cells of the genus Saccharomiyces, are commonly used in both laboratory research and industrial-scale protein production. Yeast cells have a long history of use in the production of products for human consumption and are relatively inexpensive to culture. Methods for transforming yeast cells with exogenous DNA and producing recombinant proteins therefrom are known in the art. Lithium acetate transformation is disclosed by Gietz et al., *Yeast* 11:355–360, 1995; Schiestl and Gietz, *Curr. Genet.* 16: 339–346, 1989; and Schiestl et al., *Methods: A companion to Methods Enzymol.* 5:79–85, 1993. Additional methods are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by a selectable marker, commonly drug resistance, the ability to grow in the absence of a particular nutrient (e.g., leucine), or the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia methanolica, Pichia pastoris, Pichia guillermondii* and *Candida maltosa* are known in the art. See, for example, Gleeson et al., *J. Gen. Microbiol.* 132:3459–3465, 1986; Faber et al., *Yeast* 11:1331–1344, 1995; Cregg, U.S. Pat. No. 4,882,279; Stroman et al., U.S. Pat. No. 4,879,231; and Raymond, U.S. Pat. Nos. 5,716,808 and 5,736,383.

Other fungal cells are also suitable as host cells. For example, Aspergillus cells can be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

Methods for producing recombinant proteins in cultured mammalian cells are known in the art. Exogenous DNA is introduced into mammalian host cells by, for example, calcium phosphate-mediated transfection (Wigler et al., Cell 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., eds., *Current Protocols in Molecular Biology,* John Wiley and Sons, Inc., NY, 1987), or liposome-mediated transfection (Hawley-Nelson et al., *Focus* 15:73, 1993; Ciccarone et al., *Focus* 15:80, 1993). The production of recombinant proteins in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Preferred cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

Insect cells can be infected with recombinant baculovirus vectors, which are commonly derived from *Autographa californica* multiple nuclear polyhedrosis virus (AcMNPV). DNA encoding the polypeptide of interest can be inserted into the viral genome in place of the polyhedrin gene coding sequence by homologous recombination. The donor DNA is operably linked to the polyhedrin gene promoter, terminator, and flanking sequences. The resulting recombinant virus is used to infect host cells, typically a cell line derived from the fall armyworm, *Spodoptera frugiperda*. See, in general, Glick and Pasternak, Molecular Biotechnology: Principles and Applications of Recombinant DNA, ASM Press, Washington, D.C., 1994. See also, Guarino et al., U.S. Pat. No. 5,162,222 and WIPO publication WO 94/06463.

Prokaryotic host cells, including strains of the bacteria *Escherichia coli*, Bacillus and other genera are also useful as host cells. Techniques for transforming these hosts and expressing foreign DNA sequences cloned therein are well known in the art (see, e.g., Sambrook et al., ibid.). When expressing a polypeptide of interest in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

The use of *Pichia methanolica* as host for the production of recombinant proteins is disclosed in WIPO Publications WO 97/17450, WO 97/17451, WO 98/02536, and WO 98/02565; and U.S. Pat. Nos. 5,716,808 and 5,736,383. DNA molecules for use in transforming *P. methanolica* will commonly be prepared as double-stranded, circular plasmids, which are preferably linearized prior to transformation. For polypeptide production in *P. methanolica,* it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (T) of from 1 to 40 milliseconds, most preferably about 20 milliseconds.

Transformed or transfected host cells, including fungal cells, bacteria, and mammalian cells, are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally be formulated to select for cells containing the exogenously added DNA as known in the art and disclosed above. For example, *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium is YEPD (2% D-glucose, 2% Bacto™ Peptone (Difco Laboratories, Detroit, Mich.), 1% Bacto™ yeast extract (Difco Laboratories), 0.004% adenine, 0.006% L-leucine). The cells may be passaged by dilution into fresh culture medium or stored for short periods on plates under refrigeration. For long-term storage, the cells are preferably kept in a 50% glycerol solution at −70° C.

Proteins prepared using expression vectors of the present invention can be recovered from the host cells, including recovery from cell lysates and cell-conditioned culture media. In most cases it is preferred to then purify the proteins to ≧80% purity, more preferably to ≧90% purity, even more preferably ≧95% purity. Proteins for use in pharmaceutical applications will be purified to a pharmaceutically pure state, that is greater than 99.9% pure with respect to contaminating macromolecules, particularly other proteins and nucleic acids, and free of infectious and pyrogenic agents. Methods for purifying proteins produced in recombinant host cells are known in the art, and include salt fractionation, affinity chromatography, ion-exchange chromatography, hydrophobic interaction chromatography, and other methods. See, in general, Scopes, *Protein Purification: Principles and Practice,* Springer-Verlag, New York, 1994. Proteins comprising affinity tags can be purified by affinity chromatography on the cognate ligand. For example, a protein comprising a polyhistidine affinity tag (typically about 6 histidine residues) can be purified by affinity chromatography on a nickel chelate resin. See, for example, Houchuli et al., Bio/Technol. 6: 1321–1325, 1988.

The invention is illustrated by the following non-limiting examples.

EXAMPLES

Example 1. Preparation of DNA

Protein expression acceptor vectors with the appropriate yeast and *E. coli* replication sequences were constructed for expression of proteins in mammalian cells and in *Pichia methanolica* as shown in Table 1. These vectors were designed so that proteins could be expressed in their native forms, or with N-terminal or C-terminal FLAG™ (Hopp et al., ibid.; available from Eastman Kodak Co., New Haven, Conn.) or Glu-Glu (Grussenmeyer et al., ibid.) affinity tags.

TABLE 1

| Plasmid | Host | Tags* |
| --- | --- | --- |
| pCZR198 | mammalian | native, N or C FLAG ™ |
| pCZR199 | mammalian | native, N or C Glu—Glu |
| pCZR202 | Pichia | native, αFpp, |
|  |  | αFpp + N or C FLAG ™ |
| pCZR204 | Pichia | native, αFpp, |
|  |  | αFpp + N or C Glu—Glu |

*N or C Flag ™ indicates FLAG ™ tag positioned at the N- or C-terminus of the polypeptide of interest N or C Glu—Glu indicates Glu—Glu tag (SEQ ID NO:1) at the N- or C-terminus of the polypeptide of interest αFpp indicates *S. cerevisiae* α-factor prepro peptide Strategies for obtaining a series of mammalian cell constructs are shown in FIG. 4. These constructs are designed to direct secretion of the protein of interest using either its native leader or the leader from tissue plasminogen activator (tpa).

The precise sequences (coding strand only) surrounding the mammalian cell cloning sites are shown in SEQ ID NO:2 and SEQ ID NO:3. SEQ ID NO:2 is a portion of pCZR198, a plasmid designed for expression of N-terminally and C-terminally FLAGTM-tagged proteins in mammalian cells. SEQ ID NO:2 comprises a 5' tpa leader sequence followed by two FLAG™ sequences (nucleotides 52 to 75 and 82 to 105) flanking a Sna Bl restriction site (TACGTA). SEQ ID NO:3 is a portion of pCZR199, a plasmid designed for expression of N-terminally and C-terminally Glu-Glu tagged proteins in mammalian cells. SEQ ID NO:3 comprises a 5' tpa leader sequence followed by two Glu-Glu sequences (nucleotides 55 to 72 and 82 to 99) flanking a Sna B1 restriction site.

The precise sequences (coding strand only) surrounding the Pichia expression plasmid cloning sites are shown in SEQ ID NO:4 and SEQ ID NO:5. SEQ ID NO:4 is the sequence surrounding the blunt-ended SmaI cloning site in the FLAG™ tag expression vector pCZR202. This sequence encodes five residues of *S. cerevisiae* α-factor pre-pro sequence, including the Lys-Arg KEX2 protease cleavage site, and N- and C-terminal FLAG™ tags (nucleotides 16–39 and 58–81), and further includes a SmaI site (CCCGGG) and a *P. methanolica* AUG1 terminator. SEQ ID NO:5 is the sequence surrounding the blunt-ended SmaI cloning site in the Glu-Glu tag expression vector pCZR204. This sequence encodes five residues of *S. cerevisiae* α-factor pre-pro sequence, including the Lys-Arg KEX2 protease cleavage site, and N- and C-terminal Glu-Glu tags (nucleotides 22–39 and 61–78), and further includes a SmaI site and an AUG1 stop codon.

Double-stranded DNA linkers were generated from their constituent oligonucleotides as shown in FIG. 3 using the polymerase chain reaction (PCR; see, for example, Mullis, U.S. Pat. No. 4,683,202). Two linkers are required for each recombination reaction. In a typical synthesis, PWO polymerase (Boehringer Mannheim, Indianapolis, IN) in manufacturer's supplied buffer is combined with 1 pmol of central oligonucleotides and 100 pmol of primers in a 100 µl reaction that is run for 10 cycles of 94° C.-30 sec; 50° C.-60 sec; 72° C.-60 sec. Such a reaction typically generates 2–4 Ag of double-stranded linker. Linker size, quantity and quality are evaluated on TBE (10×TBE is 108 g/L Tris base, 55 g/L boric acid, 8.3 g/L disodium EDTA) gels containing 2–3% agarose. Linkers are concentrated to a final concentration of 10 µg/µl by ethanol precipitation and resuspension in $H_2O$.

Common oligonucleotides and primers for mammalian and Pichia expression plasmids were designed and synthesized (SEQ ID NOS:6–23). These oligonucleotides and primers are described below in Table 2.

TABLE 2

| oligonucleotide number | SEQ ID NO. | Description |
| --- | --- | --- |
| 14,396 | 6 | Sense primer to amplify 5' N-terminal FLAG or Glu-Glu tag linker sequence encoding tpa leader and tag |
| 14,391 | 7 | Sense central oligonucleotide to amplify 5' N-terminal FLAG tag linker sequence encoding tpa leader and tag |
| 14,397 | 8 | Sense central oligonucleotide to amplify 5' N-terminal Glu-Glu tag linker sequence encoding tpa leader and tag |
| 14,455 | 9 | Antisense central oligonucleotide to amplify 3' N-terminal FLAG or Glu-Glu tag linker sequence encoding sequences just downstream of the stop codon and 3' XbaI or SpeI or AvrII or NheI site |
| 14,394 | 10 | Antisense primer to amplify 3' N-terminal FLAG or Glu-Glu tag linker sequence encoding sequences just downstream of the stop codon and 3' XbaI or SpeI or AvrII or NheI site |
| 14,454 | 11 | Sense primer to amplify 5' C-terminal FLAG or Glu-Glu tag linker sequence encoding sequences just upstream of endogenous Kozak sequence and ATG |
| 14,392 | 12 | Sense central oligonucleotide to amplify 5' C-terminal FLAG or Glu-Glu tag linker sequence encoding sequences just upstream of endogenous Kozak sequence and ATG |
| 14,390 | 13 | Antisense central oligonucleotide to amplify 3' C-terminal FLAG tag linker sequence encoding tag, stop codon, XbaI site and 3' terminator sequences |
| 14,393 | 14 | Antisense central oligonucleotide to amplify 3' C-terminal Glu-Glu tag linker sequence encoding tag, stop codon, XbaI site and 3' terminator sequences |

TABLE 2-continued

| oligonucleotide number | SEQ ID NO. | Description |
| --- | --- | --- |
| 14,395 | 15 | Antisense primer to amplify 3' C-terminal Flag or Glu-Glu tag linker sequence encoding tag, stop codon, XbaI site and 3' terminator sequences |
| 13,497 | 16 | Sense common primer for N-terminal linker |
| 13,731 | 17 | Sense common central oligonucleotide for N-terminal linker |
| 15,633 | 18 | Antisense common oligonucleotide for C-terminal linker |
| 13,734 | 19 | Antisense common primer for C-terminal linker |
| 14,822 | 20 | Sense common primer for N-terminal linker |
| 14,821 | 21 | Sense common central oligonucleotide for N-terminal linker |
| 15,632 | 22 | Antisense common oligonucleotide for C-terminal linker |
| 14,820 | 23 | Antisense common primer for C-terminal linker |

Exemplary N-terminal tag linkers are generated using the following combinations of common oligonucleotides from Table 2: 14,396 (SEQ ID NO:6) and 14,391 (SEQ ID NO:7); 14,396 (SEQ ID NO:6) and 14,397 (SEQ ID NO:8); and 14,394 (SEQ ID NO:10) and 14,455 (SEQ ID NO:9). Exemplary C-terminal tag linkers are generated using common oligonucleotides 14,454 (SEQ ID NO:11) and 14,392 (SEQ ID NO:12); 14,395 (SEQ ID NO:15) and 14,390 (SEQ ID NO:13); and 14,395 (SEQ ID NO:15) and 14,393 (SEQ ID NO:14). In each case, these common oligonucleotides are used in combination with construct-specific oligonucleotides designed to provide the necessary sequence overlap with the acceptor plasmid. For ease of recloning, these construct-specific oligonucleotides should include restriction sites.

Example 2. Transformation of yeast

For a typical recombinatorial transformation, 1 µg of donor fragment (cDNA), 1 µg of each linker, and 0.1 µg of acceptor vector are mixed in a volume not exceeding 10 µl and added to a 100 µl aliquot of previously frozen electrocompetent yeast cells. The *Saccharomyces cerevisiae* yeast strain SF838-9Dα (Matα, ade6, his4, leu2, ura3, pep4; disclosed by Rothman et al., *EMBO J.* 8:2057–2065, 1989) is preferred. It is prudent to include a mock tranformation (vector alone) to evaluate the efficiency of recombination. The cells are electropulsed and plated on selective media lacking uracil. Subsequently, plasmids harbored in yeast are transferred to *E. coli*, and $Amp^R$ colonies are screened for the desired constructs.

Two protocols for the preparation of competent yeast cells are disclosed below. The first protocol is simpler to use. The second protocol yields more competent cells and more consistent transformation efficiencies. For either protocol, fresh cultures of cells that are actively proliferating in the early log phase of growth are used for preparation of electrocompetent cells. Use of fresh cultures has been found to maximize transformation efficiency.

The first method is based on that of Becker and Guarente (*Methods Enzymol.* 194:182–87, 1991). On day 1, *S. cerevisiae* yeast strain SF838-9D is streaked on two to four YEPD plates and incubated at 30° C. for ~24 hours. On day 2, two to four plates of cells are resuspended in 5 ml of YEPD broth. The resuspended cells are used to inoculate 200 ml of YEPD broth (in a 1000 ml baffled shake flask) to a final $OD_{600}$ of <0.1. The culture is shaken vigorously at 30° C. for 4–6 hours. While the culture is shaking 500 ml $H_2O$ and ~50 ml of 1.2M sorbitol are chilled on ice. The cells are harvested in a 250 ml centrifuge bottle at 5000 rpm for 1–2 minutes. The cells are then resuspended in 200 ml ice-cold $H_2O$, pelleted again, resuspend in 200 ml cold $H_2O$, pelleted, resuspend in 20 ml 1.2M sorbitol, pelleted, and resuspended in 1 ml 1.2M sorbitol. 100-μl aliquots of cell suspension can be used immediately for transformation, or frozen in 100 μl aliquots at −70° C. for later use.

For transformation, DNA fragments in no more than 10 μl of total volume are mixed with 100 μl electrocompetent cells and transferred to a 0.2 cm electroporation cuvette. The mixture is pulsed at 1.5 kV and 200 ohms. Several cuvettes can be pulsed prior to plating. To plate cells, 600 μl of 1.2 M sorbitol is added to each cuvette, the cuvette contents are mixed, and two 300 μl aliquots are plated on two URA D plates (Table 3) that are subsequently incubated at 30° C. Transformants are seen after 48 hours. Transfer of plasmids from yeast to *E. coli* is described in Example 3.

TABLE 3

ADE D 0.056% -Ade -Trp -Thr powder
0.67% yeast nitrogen base without amino acids
2% D-glucose
0.5% 200× tryptophan, threonine solution

URA D 0.056% -Ura -Trp -Thr powder
0.67% yeast nitrogen base without amino acids
2% D-glucose
0.5% 200× tryptophan, threonine solution -Ura -Trp -Thr powder powder made by combining 4.0 g adenine, 3.0 g arginine, 5.0 g aspartic acid, 2.0 g histidine, 6.0 g isoleucine, 8.0 g leucine, 4.0 g lysine, 2.0 g methioine, 6.0 g phenylalanine, 5.0 g serine, 5.0 g tyrosine, and 6.0 g valine (all L- amino acids)

-Ade -Trp -Thr powder powder made by combining 3.0 g arginine, 5.0 g aspartic acid, 2.0 g histidine, 6.0 g isoleucine, 8.0 g leucine, 4.0 g lysine, 2.0 g methionine, 6.0 g phenylalanine, 5.0 g serine, 5.0 g tyrosine, 4.0 g uracil, and 6.0 g valine (all L- amino acids)

200× tryptophen, threonine solution 3.0% L-threonine, 0.8% L-tryptophan in $H_2O$
For plates, and 1.8% Bacto ™ agar (Difco Laboratories).

The second method is based on that of Meilhoc et al. (*Bio/Technology* 8: 223–27, 1990). *S. cerevisiae* strain SF838-9D is streaked on two to four YEPD plates and incubated at 30° C. for ~24 hours. On the second day, two to four plates of cells are resuspended in 5 ml of YEPD broth and used to inoculate 200 ml of YEPD broth (in a 1000 ml baffled shake flask) to a final $OD_{600}$ of <0.1. The culture is shaken vigorously at 30° C. for 4–6 hours. 40 ml of room temperature KD buffer (50 mM $KPO_4$, pH 7.5, 25 mM dithiothreitol (DTT), add the DTT just prior to use) and 400 ml of ice cold STM (270 mM sucrose, 10 mM Tris, pH 7.5, 1 mM $MgCl_2$) are prepared. The cells are harvested by centrifugation (e.g., 5000 RPM for 1–2 min) and resuspended in 40 ml of KD buffer. The resuspended cells are incubated at 30° C. for 15 minutes, harvested, and resuspended in 200 ml of ice-cold STM. The cells are harvested and resuspended in 100 ml of cold STM, then harvested and resuspended in 3–5 ml cold STM. At this point, the cells are electrocompetent and can either be used directly or aliquotted and frozen.

100 μl of electrocompetent cells are mixed with DNA (the volume should not exceed 10 μl) and transferred to a 0.2 cm electroporation cuvette. The cells are electropulsed at 0.75 kV (5 kV/cm), ∞ ohms, 25 μF. To plate the cells, 600 μl of 1.2 M sorbitol is added to each cuvette, the contents of the cuvettes are mixed, and two 300-μl aliquots are plated on two URA D plates that are subsequently incubated at 30° C. As disclosed by Meilhoc et al. (ibid.), a "recovery" period prior to plating may enhance transformation efficiency. Recovery is achieved by adding 1 ml YEPD to the electropulsed cells in the cuvette, transferring the cells to a 15 ml culture tube, and incubating the cells with gentle agitation at 30° C. for one hour. The cells are harvested in a microfuge set at "half" speed and resuspended in 1 ml 1× yeast nitrogen base (Difco Laboratories, Inc., Detroit, Mich.). 200 μl-aliquots are plated on URA D media, and the plates are incubated at 30° C.; proceed as above. Transformants are seen after 48 hours. Transfer of plasmids from yeast to *E. coli* is described in the following Example.

Example 3. Plasmid transfer from yeast into *E. coli*

Plasmids are transferred from yeast into *E. coli* using a protocol adapted from Hoffman and Winston, *Gene* 57:267–72, 1987. $Ura^+$ yeast transformants are resuspended from a single plate in 2.5 ml $H_2O$ and a 1.5-ml aliquot is transferred to an Eppendorf tube. The tube is spun in a microfuge at ½ speed for 10 seconds, and the water is discarded. The cell pellet is resuspended in 1000 μl of lysis buffer (2% Triton X-100, 1% SDS, 100 mM NaCl, 10 mM Tris, pH 8.0, 1 mM EDTA), and 500 μl is transferred to an Eppendorf tube that contains 300 μl acid-washed glass beads and 200 μl phenol-chloroform. The tube is vortexed for 1 minute two or three times and spun at MAX speed in a microfuge for ~5 minutes. 300 μl of the aqueous phase is then transferred to a fresh tube. 600 μl ethanol is added, the tube is spun for 10 minutes at 4° C., and the pellet is resuspended in 100 μl $H_2O$. 0.5 μl of the yeast DNA preparation is used to transform a 40-μl aliquot of frozen electrocompetent *E. coli* cells (commercially available cells or electrocompetent strain MC1061 prepared as described below). The cells are electropulsed at 2.0 kV and 400 ohms. 1 ml SOC (2% Bacto™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) is added, and the cells are allowed a 1-hour recovery at 37° C. prior to plating 250-μl aliquots on four LB AMP plates (LB broth, Lennox (Difco), 1.8% Bactotm Agar (Difco), 100 mg/L Ampicillin). Plasmid recoveries ($Amp^R$ transformants) vary from 10–1000 colonies.

Electrocompetent *E. coli* cells are prepared by inoculating 1 liter of LB broth with the *E. coli* strain of choice (e.g., strain MC1061) taken from fresh plates to an $OD_{600}$ of about 0.1. The culture is incubated with shaking at 37° C. to an $OD_{600}$ of 0.5–1.0. Cells are harvested by centrifugation at 5,000 RPM for 10 minutes and resuspended in 500 ml ice-cold, sterile $H_2O$ (it is helpful to initially suspend the pellet in a small volume, e.g., 10 ml). The cells are again harvested by centrifugation and resuspended in 250 ml ice-cold 10% glycerol. The cells are harvested at 8,000 RPM for 5 minutes and drained well, resuspended in 2.5 ml cold 10% glycerol, and the final volume is adjusted to 4 ml. 40-μl aliquots are placed in 1.5-ml tubes and frozen at −70° C.

Example 4. Screening of *E. coli* transformants for recombinant plasmids $Amp^R$ colonies harboring recombinant plasmids are screened for correct constructs by known methods. In general, PCR screening of colonies is simple and straightforward. PCR primers used to generate recombinatorial linkers can also be used to screen colonies for those harboring the correct plasmid constructs.

Recombinatorial linkers are prone to PCR generated errors (~10% of the linkers incorporated into plasmids have errors), and thus DNA constructs should be sequenced to detect mistakes. This is fairly simple in most cases, since sequencing involves reads into the first 150 base pairs of either end of a subcloned cDNA.

Example 5. Expression of zFGF-5 Polypeptide

A DNA sequence encoding zFGF-5, a fibroblast growth factor (FGF) homolog, was prepared as disclosed in WIPO Publication WO 98/16644. The open reading frame and a portion of the 3'-untranslated region are shown in SEQ ID NO:24.

ZFGF-5 is expressed in *Pichia methanolica* using the methods disclosed in WIPO Publication WO 9717450 and U.S. Pat. No. 5,716,808. An expression plasmid containing all or part of a polynucleotide encoding zFGF-5 is constructed via homologous recombination. The expression vector is built from pCZR204, which contains the AUG1 promoter, followed by the αFpp leader sequence, an amino-terminal peptide tag encoding sequence, a blunt ended SmaI restriction site, a carboxy-terminal peptide tag encoding sequence, a translational STOP codon, the AUG1 terminator, the ADE2 selectable marker, and finally the AUG1 3' untranslated region. Also included in this vector are the URA3 and CEN-ARS sequences for selection and replication in *S. cerevisisiae*, and the $Amp^R$ and colE1 ori sequences for selection and replication in *E. coli*. The zFGF-5 sequence inserted into this vector begins at residue 27 (Ala) of the zFGF-5 amino acid sequence (SEQ ID NO:25).

To construct pSDH114, a plasmid for expression of zFGF-5 in *P. methanolica*, the following DNA fragments are transformed into *S. cerevisisae:*

100 ng of the acceptor vector pCZR204 that has been digested with SmaI;

1 μg of an XbaI-SalI restriction fragment comprising zFGF-5 coding sequence;

1 μg of a synthetic, PCR-generated, double-stranded linker segment comprising 70 base pairs of the αFpp coding sequence on one end, joined to 70 base pairs of the amino-terminal coding sequence from the mature zFGF-5 sequence on the other, generated from oligonucleotides zc13,497 (SEQ ID NO:16); zc15,131 (SEQ ID NO:26); zc15,132 (SEQ ID NO:27); and zc15,134 (SEQ ID NO:28) as shown in SEQ ID NO:29; and 1 μg of of a synthetic, PCR-generated, double-stranded linker segment comprising 70 base pairs of carboxy-terminal coding sequence from zFGF-5 on one end with 70 base pairs of AUG1 terminator sequence, generated from oligonucleotides zc13,529 (SEQ ID NO:30); zc13,525 (SEQ ID NO:31); zc13,526 (SEQ ID NO:32); and zc13,528 (SEQ ID NO:33) as shown in SEQ ID NO:34. $Ura^+$ colonies are selected, and DNA from the resulting yeast colonies is extracted and transformed into *E. coli*. Individual clones harboring the correct expression construct are identified by PCR screening with oligonucleotides zc13,497 (SEQ ID NO:16) and zc13,528 (SEQ ID NO:33), followed by restriction digestion to verify the presence of the ZFGF5 insert and DNA sequencing to confirm the desired DNA sequences have been joined to one another.

Plasmid DNA is isolated for one of the correct clones, and the DNA is digested with Sfi I to liberate the Pichia expression cassette from the vector backbone. The Sfi I-cut DNA is then transformed into *Pichia methanolica* strain PMAD16 (Raymond et al., Yeast 14, 11–23, 1998), and plated on ADE D plates (Table 3) for selection. Clones are picked and screened via Western blot for high-level zFGF-5 expression.

For small-scale protein production (e.g., plate or shake flask production), *P. methanolica* transformants that carry an expression cassette comprising a methanol-regulated promoter (such as the AUG1 promoter) are grown in the presence of methanol and the absence of interfering amounts of other carbon sources (e.g., glucose). For small-scale experiments, including preliminary screening of expression levels, transformants are grown at 30° C. on solid media containing, for example, 20 g/L Bacto-agar (Difco), 6.7 g/L yeast nitrogen base without amino acids (Difco), 10 g/L methanol, 0.4 mg/L biotin, and 0.56 g/L of -Ade -Trp -Thr powder (Table 3). Because methanol is a volatile carbon source it is readily lost on prolonged incubation. A continuous supply of methanol can be provided by placing a solution of 50% methanol in water in the lids of inverted plates, whereby the methanol is transferred to the growing cells by evaporative transfer. In general, not more than 1 ml of methanol is used per 100-mm plate.

Slightly larger scale experiments are carried out using cultures grown in shake flasks. In a typical procedure, cells are cultivated for two days on minimal methanol plates as disclosed above at 30° C., then colonies are used to inoculate a small volume of minimal methanol media (6.7 g/L yeast nitrogen base without amino acids, 10 g/L methanol, 0.4 mg/L biotin) at a cell density of about $1 \times 10^6$ cells/ml. Cells are grown at 30° C. Cells growing on methanol have a high oxygen requirement, necessitating vigorous shaking during cultivation. Methanol is replenished daily (typically 1/100 volume of 50% methanol per day).

For production scale culturing, fresh cultures of high producer clones are prepared in shake flasks. The resulting cultures are then used to inoculate culture medium in a fermenter. Typically, a 500 ml culture in YEPD grown at 30° C. for 1–2 days with vigorous agititation is used to inoculate a 5-liter fermenter. The cells are grown in a suitable medium containing salts, glucose, biotin, and trace elements at 28° C., pH 5.0, and >30% dissolved $O_2$. After the initial charge of glucose is consumed (as indicated by a decrease in oxygen consumption), a glucose/methanol feed is delivered into the vessel to induce production of the protein of interest. Because large-scale fermentation is carried out under conditions of limiting carbon, the presence of glucose in the feed does not repress the methanol-inducible promoter.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for preparing a double stranded, circular DNA molecule comprising the steps of:
   (a) providing a double-stranded donor DNA fragment encoding a polypeptide of interest;
   (b) providing a double-stranded, linear acceptor plasmid having blunt first and second ends and comprising a selectable marker and replication sequence that are functional in *Saccharamyces cerevisiae*, wherein the acceptor plasmid is essentially free of DNA encoding the polypeptide of interest;
   (c) providing a first double-stranded DNA linker comprising a first segment identical in sequence to a first region of the acceptor plasmid and a second segment identical in sequence to a first region of the donor DNA fragment, wherein each of the first and second segments of the first linker is at least 10 bp in length;

(d) providing a second double-stranded DNA linker comprising a first segment identical in sequence to a second region of the acceptor plasmid and a second segment identical in sequence to a second region of the donor DNA fragment, wherein each of the first and second segments of the second linker is at least 10 bp in length; and (e) combining the donor DNA fragment, acceptor plasmid, first DNA linker, and second DNA linker in a *Saccharomnyces cerevisiae* host cell whereby the donor DNA fragment is joined to the acceptor plasmid by homologous recombination of the donor DNA, acceptor plasmid, and linkers to form a closed, circular plasmid comprising a region encoding the polypeptide of interest.

2. The method of claim 1 wherein the acceptor plasmid further comprises a transcription promoter proximal to the first end, and the donor DNA fragment is operably linked to the transcription promoter within the closed, circular plasmid.

3. The method of claim 2 wherein the acceptor plasmid further comprises a transcription terminator proximal to the second end, and the donor DNA fragment is operably linked to the transcription terminator within the closed, circular plasmid.

4. The method of claim 1 wherein the acceptor plasmid further comprises a DNA segment encoding a leader peptide or a peptide tag, positioned such that the DNA segment is operably linked to the donor DNA fragment within the closed, circular plasmid.

5. The method of claim 1 wherein the acceptor plasmid further comprises:

a promoter, a DNA segment encoding a leader peptide, and a DNA segment encoding a first peptide tag, wherein the DNA segment encoding a leader peptide is positioned between the promoter and the DNA segment encoding a first peptide tag proximal to the first end of the acceptor plasmid, and wherein the promoter, DNA segment encoding a leader peptide, and DNA segment encoding a first peptide tag are operably linked; and a DNA segment encoding a second peptide tag proximal to the second end of the acceptor plasmid.

6. The method of claim 1 wherein each of said first and second segments of said first and second linkers is at least 50 bp in length.

7. The method of claim 1 wherein the acceptor plasmid further comprises a replication sequence and a selectable marker that function in *E. coli*.

8. A method for preparing a double stranded, circular DNA molecule comprising the steps of:

(a) providing a plurality of overlapping, double-stranded donor DNA fragments which collectively encode a polypeptide of interest;

(b) providing a double-stranded, linear acceptor plasmid having blunt first and second ends and comprising a selectable marker and replication sequence that are functional in *Saccharamyces cerevisiae*, wherein the acceptor plasmid is essentially free of DNA encoding the polypeptide of interest;

(c) providing a first double-stranded DNA linker comprising a first segment identical in sequence to a first region of the acceptor plasmid and a second segment identical in sequence to a region of one of the donor DNA fragments, wherein each of the first and second segments of the first linker is at least 10 bp in length;

(d) providing a second double-stranded DNA linker comprising a first segment identical in sequence to a second region of the acceptor plasmid and a second segment identical in sequence to a region of another of the donor DNA fragments, wherein each of the first and second segments of the second linker is at least 10 bp in length; and (e) combining the donor DNA fragments, acceptor plasmid, first DNA linker, and second DNA linker in a *Saccharamyces cerevisiae* host cell whereby the donor DNA fragments are joined to the acceptor plasmid by homologous recombination of the donor DNA fragments, acceptor plasmid and linkers to form a closed, circular plasmid comprising a region encoding the polypeptide of interest.

9. The method of claim 8 wherein the acceptor plasmid further comprises a transcription promoter proximal to the first end, and the donor DNA fragments are operably linked to the transcription promoter within the closed, circular plasmid.

10. The method of claim 9 wherein the acceptor plasmid further comprises a transcription terminator proximal to the second end, and the donor DNA fragment is operably linked to the transcription terminator within the closed, circular plasmid.

11. The method of claim 8 wherein the acceptor plasmid further comprises a DNA segment encoding a leader peptide or a peptide tag, positioned such that the DNA segment is operably linked to the donor DNA fragments within the closed, circular plasmid.

12. The method of claim 8 wherein the acceptor plasmid further comprises:

a promoter, a DNA segment encoding a leader peptide, and a DNA segment encoding a first peptide tag, wherein the DNA segment encoding a leader peptide is positioned between the promoter and the DNA segment encoding a first peptide tag proximal to the first end of the acceptor plasmid, and wherein the promoter, DNA segment encoding a leader peptide, and DNA segment encoding a first peptide tag are operably linked; and a DNA segment encoding a second peptide tag proximal to the second end of the acceptor plasmid.

13. The method of claim 8 wherein each of said first and second segments of said first and second linkers is at least 50 bp in length.

14. The method of claim 1 wherein the acceptor plasmid further comprises a replication sequence and a selectable marker that function in *E. coli*.

* * * * *